(12) United States Patent
Kotlar et al.

(10) Patent No.: US 7,325,603 B2
(45) Date of Patent: Feb. 5, 2008

(54) METHODS OF WELL TREATMENT

(75) Inventors: Hans Kristian Kotlar, Forusbeen (NO); Jarle Andre Haugan, Forusbeen (NO)

(73) Assignee: Statoil USA, Stavenger (NO)

( * ) Notice: Subject to any disclaimer, the term of this patent is extended or adjusted under 35 U.S.C. 154(b) by 0 days.

(21) Appl. No.: 10/478,776

(22) PCT Filed: May 21, 2002

(86) PCT No.: PCT/GB02/02359

§ 371 (c)(1),
(2), (4) Date: Jun. 4, 2004

(87) PCT Pub. No.: WO02/095187

PCT Pub. Date: Nov. 28, 2002

(65) Prior Publication Data

US 2004/0244969 A1 Dec. 9, 2004

(30) Foreign Application Priority Data

May 21, 2001 (GB) .............................. 0112343.9

(51) Int. Cl.
*E21B 43/22* (2006.01)
(52) U.S. Cl. ........................ 166/246; 166/310; 435/262; 435/281; 507/101; 507/201
(58) Field of Classification Search .............. 166/246, 166/310; 435/262, 281; 507/101, 201
See application file for complete search history.

(56) References Cited

U.S. PATENT DOCUMENTS

| | | | | |
|---|---|---|---|---|
| 4,384,044 A | * | 5/1983 | Kim et al. ................... | 435/101 |
| 4,506,044 A | * | 3/1985 | Cox et al. ..................... | 524/27 |
| 4,743,545 A | | 5/1988 | Torobin | |
| 4,846,981 A | * | 7/1989 | Brost ........................... | 507/277 |
| 4,850,745 A | | 7/1989 | Hafer et al. | |
| 5,083,611 A | * | 1/1992 | Clark et al. .................. | 166/246 |
| 5,250,201 A | | 10/1993 | Shilo et al. | |
| 5,297,625 A | * | 3/1994 | Premuzic et al. ............ | 166/246 |
| 5,337,820 A | * | 8/1994 | Jenneman et al. ........... | 166/246 |
| 5,376,183 A | * | 12/1994 | Gatt et al. ..................... | 134/40 |
| 5,530,095 A | * | 6/1996 | Vaughn et al. ............... | 530/326 |

FOREIGN PATENT DOCUMENTS

| | | |
|---|---|---|
| EP | 0187092 | 7/1986 |
| EP | 0365390 | 4/1990 |
| WO | WO 88/00948 | 2/1998 |

OTHER PUBLICATIONS

Cannio R et al., "An autonomously replicating transforming vector for Sulfolobus solfataricus." J. Bacteriol. Jun. 1998; 180(12):3237-40.

Collins, I.R. "Scale Inhibition by Poly(amino acids)" Shared Petrotechnical Resource, Chertsey Road, Sunbury-on-Thames, Middlesex T13 7LN.

(Continued)

*Primary Examiner*—George Suchfield
(74) *Attorney, Agent, or Firm*—Needle & Rosenberg, P.C.

(57) ABSTRACT

A method is disclosed relating to the treatment of a hydrocarbon well, which method comprises administering down a bore hole thermophilic microorganisms capable of generating a well treatment chemical, in particular wherein the bore hole is a producer bore hole and the well treatment chemical is a peptide such as polyAsp; further aspects include thermophilic microorganisms which have been genetically engineered to produce a well treatment chemical and bioreactors in which microorganisms generate well treatment chemicals for application to a down hole environment.

38 Claims, 1 Drawing Sheet

OTHER PUBLICATIONS

McGovern-Traa et al. "Petroleum Geology of the Irish Sea and Adjacent areas." Geological Society Special publication No. 124,229-236. Meadows, N.S., Trueblood, S.P., Hardman, M. & McGowan, G (eds) 1997.

Ornek et al., "Pitting corrosion inhibition of aluminum 2024 by Bacillius biofilms secreteting polyaspartate or gamma-polyglutamate." Appl. Microbiol, Biotechnol. Apr. 2002; 58(5)651-7.

* cited by examiner

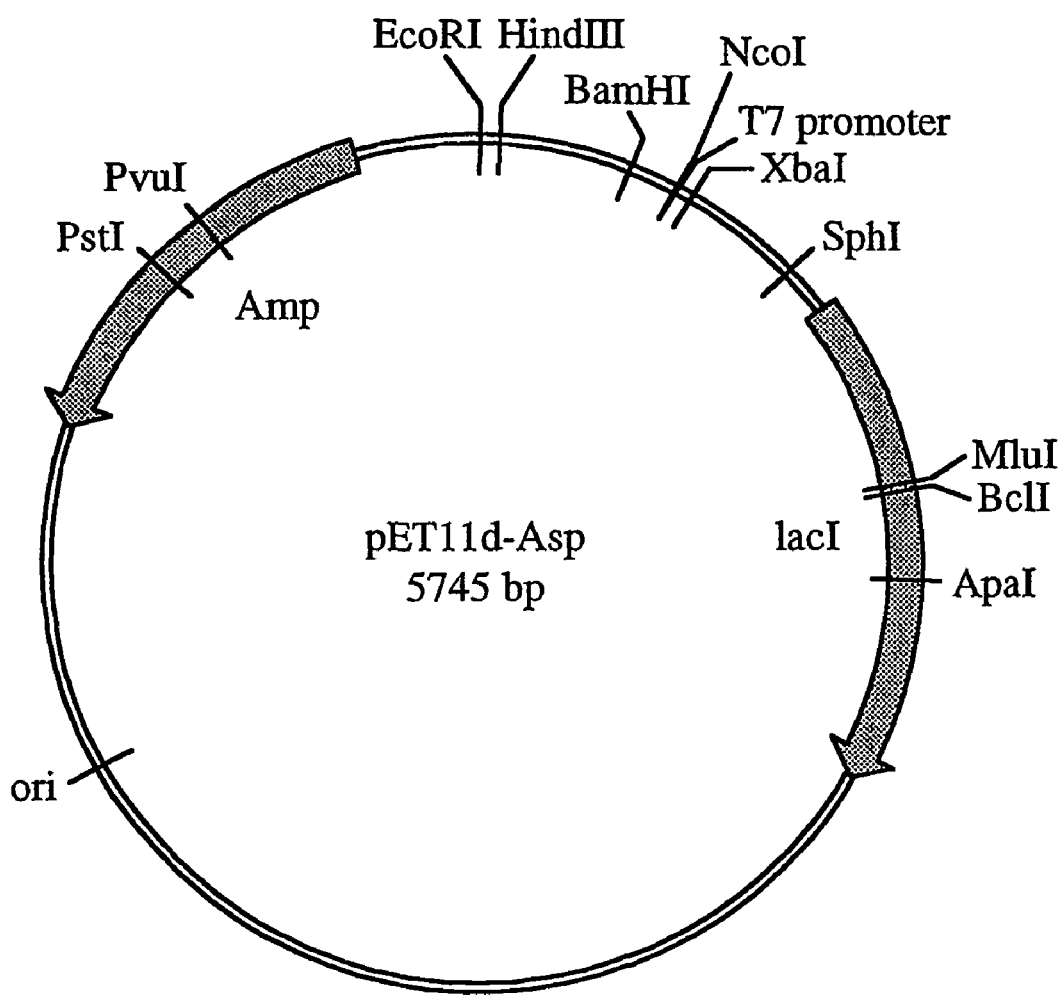

METHODS OF WELL TREATMENT

CROSS REFERENCE TO RELATED APPLICATIONS

The present application claims priority to Great Britain Application No. 0112343.9 filed May 21, 2001, which application is incorporated herein fully by this reference.

This invention relates to a method of treating a hydrocarbon well, in particular by down-hole placement of bacteria which are capable of producing well treatment chemicals or precursors or generators thereof, and to particles, compositions and structures containing these bacteria.

During the operation of a hydrocarbon well (i.e. a gas or oil well) various down-hole problems arise such as corrosion of metal fittings, hydrocarbon flow-inhibiting deposition (e.g. of scale, gas clathrates, metal sulphides, waxes, gel polymers, microbial debris, etc.), generation of toxic hydrogen sulphide by sulphate-reducing bacteria, increased water flow into the producer bore, etc.

Thus, for example, where sea water is injected through an injection bore hole into an oil-bearing stratum to drive oil through the formation (i.e. the rock) into the producer well hole, differences in solutes in the injection water and the water already present in the formation can cause metal salts to precipitate as scale so causing gradually increasing clogging of the producer well hole.

Typically this is dealt with by applying a "squeeze" of scale inhibitor chemicals, i.e. chemicals which break down the scale and increase oil or gas flow. This generally involves ceasing hydrocarbon flow, forcing an aqueous solution of the scale inhibitor down the producer bore under pressure to drive the inhibitor solution into the formation, and restarting production. Such treatment generally allows a further six or so months of hydrocarbon flow before a further squeeze is required and each squeeze causes some damage to the formation surrounding the producer bore hole and as a result an increased flow of formation fragments (i.e. rock grains etc.) into the bore.

The producer bore hole in an oil well is generally lined in the hydrocarbon bearing stratum with "gravel packs", sand containing filter elements, which serve to trap formation fragments and it has been proposed to include in such gravel packs ceramic particles coated with or impregnated with well treatment chemicals such as scale inhibitors (see EP-A-656459 and WO 96/27070) or bacteria (see WO 99/36667). Likewise treatment of the formation surrounding the producer well bore hole with well treatment chemicals before hydrocarbon production begins has also been proposed, e.g. in GB-A-2290096 and WO 99/54592.

Various polymeric, oligomeric, inorganic and other particulate carriers for well treatment chemicals are also known, e.g. ion exchange resin particles (see U.S. Pat. No. 4,787,455), acrylamide polymer particles (see EP-A-193369), gelatin capsules (see U.S. Pat. No. 3,676,363), oligomeric matrices and capsules (see U.S. Pat. No. 4,986,353 and U.S. Pat. No. 4,986,354), ceramic particles (see WO 99/54592, WO 96/27070 and EP-A-656459), and particles of the well treatment chemical itself (see WO 97/45625).

Particles coated with or containing well treatment chemicals however will inevitably only provide protection for a limited time. There is thus still a need for means of well treatment which give a prolonged period of protection, e.g. against scale or other problems, such as corrosion or hydrocarbon flow restricting problems.

In addition, one known scale inhibitor is polyaspartic acid (polyAsp). However, it is notoriously difficult to product poly (aspartic acid), on a scale which is viable for industry. The chemical synthesis of polyAsp occurs via, for example, thermal polymerisation from maleic anhydride and a phosphoric acid catalysed route. Chemical synthesis leads to the $\alpha$, $\beta$ form of the polymer rather than a form found in the natural environment. Chemical synthesis also produces by-products. The present invention therefore seeks to provide a new way of generating and using polyAsp in the downhole environment.

We now propose to effect well treatment by introducing down hole thermophilic Archea or other thermophilic bacteria or organisms capable of generating well treatment chemicals.

Archea are one of the three systems of organisms on earth, the other two being eubacteria and eukaryotes (see Howland (Ed) "The Surprising Archaea" Oxford University Press, 2000). Archea can be split into three groups: a) anaerobic methaneogens; b) anaerobic and aerobic sulphur-metabolizing bacteria (e.g. Sulfolobales and Thermoproteales); and c) moderately thermophilic Thermoplasmales. Few of group a) but most of group b) are thermophilic, being capable of surviving at temperatures as high as 90-150° C. The current edition of Bergey's Manual or Howland (Ed) (supra) can be consulted for a suitable definition and classification of Archea. Generally, Archea can be identified by their cell wall which lacks a peptidoglycan skeleton and by their cytoplasmic membrane which contains glycerol ethers with $C_{20}$ (phytanyl) and $C_{40}$ (biphytanyl) alkyl isoprenoids in place of the fatty acid glycerol esters. In addition, the DNA-dependent RNA polymerases of Archea differ from those of eubacteria in that they consist of more than four subunits and are resistant to the antibiotics rifampicin and streptolycligin.

Viewed from one aspect the invention provides a method for the treatment of a hydrocarbon well which method comprises administering down a producer bore hole thermophilic Archea or other thermophilic bacteria or microorganisms capable of generating well treatment chemicals. Suitable microorganisms will be halophilic and anaerobic as well as thermophilic, e.g. some sulphur reducing bacteria like *Desulfovibrio*-, *Desulfobulbus*-, *Desulfobacter*, *Desulfococcus*-strains etc., different *Bacillus* species, *Clostridium* species, *Thermoanaerobacter*, *Thermoanaerobium*, *Thermobacteroides*, *Thermodesulfobacterium*, some *Pseudomonas* etc. Some sulphur reducing bacteria may also use other metabolic pathways through lactate or acetate. These Archea or other thermophilic organisms may be naturally occurring but typically they will have been genetically modified to produce well treatment chemicals. Archea, particularly genetically modified Archea, being preferred for use in the methods of the invention. In a particularly preferred embodiment, the well treatment chemicals will be agents which inhibit scale.

Thermophilic bacteria have generally been considered to be a problem in oil wells as they are usually sulphur-metabolizing and generate toxic hydrogen sulphide.

As stated above, according to the present invention it is proposed to administer microorganisms down a producer bore hole and thus the invention is not concerned with administering microorganisms down an injection hole. The conditions in the two holes are very different both in terms of the physical environment and the drilling problems faced. Thus, an effective treatment method in one hole would likely not be appropriate for the other. Similarly microorganisms which could thrive in the environment of one hole would not necessarily survive in the other.

The microorganism used is preferably one indigenous to the hydrocarbon field in which the well to be treated is located. Methods are described herein for the sampling and identification of suitable indigenous microorganisms which may be utilised in the methods of the invention. However other Archea, such as those deposited at the American Type Culture Collection (ATCC), the Deutsche Sammlung von Mikroorganismen (DSM) and the British Collection of Industrial and Marine Bacteria (CIMB) may be used.

Examples of suitable species include: *Desulfotomaculum, Archaeoglobus* (e.g. *A. fulgidis*), *Thermodesulforabdus, Petrofaga* (e.g. *P. mobilis*), *Methanococous* (e.g. *M. thermolithotrophus*), *Thermodesulfotobacteria, Sulfolobales, Thermoprotealis, Thermoplasmales*. Members of all the previously mentioned groups of Archea may be used in the methods of the present invention, provided they display the necessary thermophilic character.

Archea and other bacteria or microorganisms which can survive at temperatures in excess of 50° C. (more preferably in excess of 70° C.) can be considered "thermophilic". Such microorganisms, especially Archea which can thrive at temperatures in excess of 90° C. are especially preferred.

The Archea and other bacteria or microorganisms may conveniently be facultative anaerobic/strict anaerobic and have very simple nutrition requirements. This is particularly important as it may be necessary to introduce the bacteria and nutrients therefor into the down hole environment, for example in a porous matrix. The Archea and other bacteria or microorganisms may conveniently use short chain hydrocarbon or acetate in their energy metabolism. The desired nutrients may conveniently be introduced into the porous matrix or co-injected with the bacteria or other microorganisms in porous particles.

The Archea and other bacteria or microorganisms may be genetically modified by standard techniques to introduce operative nucleic acid sequences coding for proteins which are well treatment chemicals or which participate in the production of chemicals suitable for use in well treatment chemicals. Thus, the bacteria may produce the well treatment chemicals directly or they may produce precursors or generators of well treatment chemicals. It is possible that according to the genetic modification it is a regulatory rather than a coding sequence which is introduced into the host organism and is responsible for switching on or enhancing expression of a relevant coding sequence.

The following references and others from the 3rd International Congress on extremophiles, Sep. 3-7, 2000, Technical University Hamburg-Harburg may be consulted regarding transformation of the Archea:

L27: "Phylogenetic Patterns of Posttranscriptional Modification in Ribosomal RNA of Thermophiles", Crain, P. F.; Noon, K. R.; Stetter, K. O. and McCloskey, J. A. from the University of Utah;

P132: "Overexpression in *Escherichia coli* of the Gene Coding for Glucose Dehydrogenase from Haloferax mediterranei", Esclapez, J.; Pire, C.; Ferrer, J. and Bonete, M. J. from the University of Alicante;

P122: "Molecular Cloning of an Extremely Thermostable Esterase Gene from the Hyperthermophilic Archaeon *Sulfolobus solfataricus* by Expression in *Escherichia coli*", Morana, A.; Aurilia, V.; Di Prizito, N. and Cannio, R. from Istituto di Scienze dell'Alimentazione, Consiglio Nazionale delle Ricerche (CNR);

L52: "A Genetic System for the Hyperthermophilic Archaeon *Pyrococcus* abyssi: Spheroplasts Transformation and Construction of a Shuttle Vector", Lucas, S.; Toffin, L.; Zivanovic, Y.; Forterre, P.; Charlier, D. R.; Prieur, D. and Erauso, G. from Universite Paris-Sud.

References hereinbelow to 'Archea' apply mutatis mutandis to other thermophilic bacteria or microorganisms which may be introduced down hole in accordance with the present invention.

For expression of exogenous genes in Archea a number of vectors have been described and used in the prior art. For example Cannio et al (1998, J. Bacteriol. 180(12): 3237-40) describe a vector that is particularly efficient in *Sulfolobus solfataricus*. Cannio et al further describe methods and vectors for transforming Archae in the Journal "Extremophiles" 2001 5(3):153-9. Shuttle vectors that are suitable for use in *E. Coli* and *Sulfolobus* have also been made (Cannio et al, first meeting on Extremophiles as cell Factories, Athens, 19-21 Apr. 1997). These papers are incorporated herein by reference. Modifications to these vectors which may be desirable for use with other species of microorganism are known in the art and within the competence of the worker in this area.

A method for transforming an Archea which comprises introducing into said Archea a nucleic acid molecule, expression of which directly or indirectly results in production, typically by the Archea itself, of a well treatment chemical comprises a further aspect of the invention.

Archea which have been genetically modified to produce well treatment chemicals comprise a further aspect of the present invention. The treatment chemical produced by the Archea will be of use in a producer hole environment and the Archea capable of surviving in that environment.

Thus, genes encoding useful well treatment chemicals or enzymes or other factors involved in the production of active well treatment chemicals from one organism can be introduced using suitable transformation techniques well known in the art, into the host Archea.

General guidance on cloning techniques can be found, for example, in the Molecular Cloning laboratory manual by Maniatis et al. published by the Cold Spring Harbour Laboratory Press. More specifically, reference L52 shows how transformation can be achieved in the hyper-thermophilic Archea *Pyrococcus abyssi*, for example.

Suitable gene provider organisms may be other bacteria or microorganisms or higher eukaryotes including plants and mammals. The expression product should be stable in down hole conditions and thus may typically be thermostable. Thus, target organisms to provide the gene of interest may themselves exist in rather extreme environments. The gene introduced into the Archea may have been modified to enhance the thermostability of the expression product. Moreover, proteins expressed by organisms which themselves could not survive down hole may be sufficiently stable to survive in active form when expressed by the thermophilic Archea. The protein may also contain further modification, such as the addition of tags, e.g. his tags or myc tags which enhance the isolation of the protein from the system, if this is required.

For some of the simpler well treatment chemicals, for example poly-amino acids such as polyaspartate, the nucleic acid encoding the gene may be synthesised de novo (i.e. not taken from another organism) and introduced into the Archea in the normal way.

Transformation will typically involve a plasmid vector which will also contain a gene to enable identification of successfully transformed Archea, e.g. a gene for antibiotic resistance such as chloramphenicol acetyltransferase. When the microorganism is introduced down hole, the antibiotic could also be introduced, e.g. the organism, nutrients and antibiotic could be co-injected in porous particles. In this way endogenous bacteria may be knocked out giving a competitive growth advantage to the modified organism. Other methods for selecting transformants are known to the skilled man and include the use of a light sensitive vector, a lux-gene, which causes positive colonies to light up in the dark. Other suitable vehicles for transformation of the bacteria include cosmids and bacteriophage molecules.

As is well understood in the art, the gene introduced into the Archea must be operably linked to control sequences which are compatible with normal gene expression in the Archeal host. Control sequences induce promoters and optionally regulatory sequences which cause a gene to be turned on or off in response to a chemical or physical stimulus. The gene may insert into the Archeal chromosome and may be regulated by endogenous control sequences or if the vector does not insert, then the gene of interest will be co-transfected with suitable regulatory and promoter sequences.

It may be necessary to supply to the Archea amino acids, co-factors etc. required in the production of the well-treatment chemicals.

Examples of simple non-natural well treatment chemicals that may be produced in this way include aspartate rich or aspartate repeat containing polypeptides and oligopeptides and aspartic acid polymers and oligomers which can function as scale inhibitors.

An especially preferred group of scale inhibitors are molecules which are rich in amino acids having charged side chains, particularly anionic amino acids such as aspartic or glutamic acid but also including cationic amino acids such as lysine, arginine or histidine. Such molecules incorporating non-genetically coded charged amino acids may be synthesised in situ by the Archea, although molecules which can be generated by translation and thus comprise only the 20 genetically coded amino acids are preferred.

Thus the well treatment chemical may be a peptide (no distinction is made herein between 'peptide' and 'polypeptide') which is rich in charged, particularly in acidic, amino acids. Such a peptide may be comprised entirely of charged amino acids or an effective proportion of charged amino acids; e.g. over its length or a part thereof between 30 preferably between 50 and 100% of all amino acids will be charged e.g. 60, 70, 80 or 90% of all amino acids will be charged. If the peptide has a charged part, this part will comprise at least 10 amino acid residues, preferably 15 or more residues having a proportion of charged, preferably acidic residues as discussed above. In absolute terms the well treatment peptide will preferably have at least 3, preferably 4 or more, more preferably 6 or more e.g. 8-14 charged residues or 15 to 25 charged residues, particularly 20 to 25 charged residues. Charged residues may be consecutive or be separated by other non-charged residues but there will generally be a clearly charged nature to the peptide or a region/part thereof.

The polymer may be a copolymer e.g. of aspartic acid and histidine, glycine, alanine, proline, leucine, serine or tyrosine. It has been shown that copolymers of aspartic acid and proline or histidine can be even more efficient scale inhibiting polymers than polymers of aspartic acid alone. The non-charged residues are preferably proline. Although the presence of methionine at the N terminus of the peptide may also occur.

The charged polypeptide is most preferably polyAsp. Reference herein to "polyAsp" includes copolymers as discussed above but in each case at least 30% preferably at least 50% e.g. at least 70% of the residues in the final peptide product are aspartic acid. Initiation of translation will require another residue in the first position (derived from the start codon) of the initially expressed peptide, typically this will be Met although bacteria may also use other residues in the first position. The final polyAsp product used in the well treatment may retain the initiating residue or this may be cleaved, particularly where the polyAsp gene incorporates an upstream signal or other sequence. The polyAsp product (excluding any signal or tag sequences) will typically be 15-75 amino acids in length e.g. 20-45 amino acids in length and will preferably incorporate 1-8 e.g. 2-4 proline residues.

The production of polyAsp from a natural renewable source such as Archea or Bacteria either in situ in the well or in a bioreactor provides an efficient means of producing large quantities of polyAsp. Thus use of Archea or bacteria to produce polyAsp is also more environmentally friendly than any current method. The production of polyAsp may either take place in situ, as described elsewhere in the application, via its expression in genetically modified thermophilic Archea, or alternatively may occur in a bioreactor.

The well treatment chemical may comprise a protein molecule, for example a normally expressed Archeal protein which has been modified to increase its number of charged residues. Either by increasing the number of charged, preferably acidic residues found throughout the molecule but more preferably by adding a charged region to the molecule. Thus the expressed protein may conveniently have a charged domain not found in the native molecule. This charged domain will preferably be on the exterior of the protein molecule so that it is available and able to exert its scale inhibiting properties.

The protein or the polypeptide may be excreted by the Archea or may remain attached to the bacterial cell surface. Larger proteins may traverse the cell wall, having their charged domains on the exterior of the Archea. It is possible to modify the secretion of a peptide by adding or removing signal peptides that direct the peptide to be secreted. Signal peptides for secretion or membrane localisation are well known in the art. The signal peptides may be cleaved during or after the secretion process or they may remain attached to the peptide molecule. When a signal sequence is cleaved in this way it is possible to conveniently remove the initiating Met residue. Reference herein to "polyAsp" molecules includes reference to molecules which incorporate such signal sequences, such as the APR (alkaline protease) signal sequence.

Many suitable peptidic scale inhibitor molecules will be new and these molecules constitute a further aspect of the present invention. Nucleic acid molecules which comprise a nucleotide sequence which encodes or is complementary to a sequence which encodes these peptidic scale inhibitor molecules constitute a further aspect of the present invention. A genetic construct comprising such nucleic acid molecules operably linked to a promoter sequence is a still further aspect of the present invention.

An example of a nucleic acid encoding a well treatment chemical is 5'-CATGGATGACGATGATGACCCGGAT-GATGACGACGATGACGATGACGATCCGGACG ATGACGACGATGATGACGATGATCCTAG-GCATCACCATCACCATCATTAAG-3'. Nucleic acid molecules comprising this sequence and polypeptides incorporating the amino acid sequence encoded by it, MDDDDDPDDDDDDDDPD-DDDDDDDPRHHHHHH, comprise further aspects of the invention, as does the vector pET11d-Asp as described in Example 2. Variants and fragments of these sequences which are similarly rich in Asp residues (or the triplets coding therefor, as appropriate) are further aspects of the invention. It may be preferred to design the polyAsp gene such that the different triplets coding for Asp are incorporated to avoid self-annealing although this problem can be avoided by using dsDNA.

Particular variants of interest are those which lack the C-terminal H is residues (and the linking Arg). If the polyAsp is fused to a signal sequence it will typically lack its own initiation codon and therefore not incorporate the four 5' bases CATG.

Other useful well treatment chemicals which may be produced by the Archea include alcohols and glycerols, proteinaceous and non-proteinaceous anti-freeze molecules and biosurfactants.

The invention further includes the use of naturally occurring organisms i.e. organisms which have not been genetically modified and are preferably indigenous to the oil reservoir or bore hole. Such organisms have evolved to deal specifically with the conditions found at these locations and may produce products that are useful in the invention. Such products include organic acids that protect against carbonate, cryoprotein that act against hydrates (e.g. gas hydrate which is a crystalline solid made up of a gas molecule surrounded by a cage of water molecules) and enzymes that break S-S bridges to lower viscosity. Examples of such organisms include Archea which are extremophiles, i.e. extreme thermophiles.

The Archea may be delivered to the down hole site in or on particles, e.g. porous inorganic particles (e.g. Silica, alumina etc.) or polymeric particles or in capsules, e.g. colloids, etc. These carrier particles may also carry bacterial nutrients.

Viewed from a further aspect the invention provides particles impregnated with thermophilic Archea capable of generating well treatment chemicals, preferably Archea genetically modified to produce well treatment chemicals.

Viewed from another aspect the invention provides the use for the manufacture of hydrocarbon well treatment compositions of thermophilic Archea capable of generating well treatment chemicals, preferably Archea genetically modified to produce well treatment chemicals.

Viewed from a still further aspect the invention comprises a hydrocarbon well treatment composition comprising a carrier liquid containing thermophilic Archea capable of generating well treatment chemicals, preferably Archea genetically modified to produce well treatment chemicals.

Viewed from a yet further aspect the invention comprises a tubular filter for down-hole placement containing thermophilic Archea capable of generating well treatment chemicals, preferably Archea genetically modified to produce well treatment chemicals.

In the method of the invention the bacteria may be placed down hole before and/or after hydrocarbon production (i.e. extraction of oil or gas from the well) has begun. Preferably the bacteria are placed down hole before production has begun, especially in the completion phase of well construction.

The bacteria may be placed within the bore hole (e.g. in the hydrocarbon bearing strata or in ratholes) or within the surrounding formation (e.g. in fissures or within the rock itself). In the former case, the bacteria are conveniently impregnated into particles contained within a tubular filter, e.g. a gravel pack or a filter structure as disclosed in EP-A-656459 or WO 96/27070; in the latter case, the bacteria (optionally impregnated into particles) are preferably positioned by squeezing a liquid composition containing the bacteria down the bore hole. Preferably, before production begins the bacteria are placed both within the bore in a filter and within the surrounding formation. The bacteria are alternatively inoculated into the particles.

Where the bacteria (typically impregnated into particles) are placed within the surrounding formation, the pressure used should be sufficient to cause the bacteria to penetrate at least 1 m, more preferably at least 1.5 m, still more preferably at least 2 m, into the formation. If desired, the bacteria may be applied in conjunction with porous particles to achieve a penetration of about 2 m or more into the formation. Compositions comprising such small, porous particles and bacteria according to the invention, which may be co-bladed with nutrients, form a further aspect of the invention.

Particles soaked or loaded (also referred to herein as impregnated) with Archea according to the invention advantageously have mode particle sizes (e.g. as measured with a Coulter particle size analyser) of 1 µm to 5 mm, more preferably 10 µm to 1000 µm, especially 250 to 800 µm. For placement within the formation, the mode particle size is preferably 1 to 50 µm, especially 1 to 20 µm e.g. 1-5 µm. For any particular formation, formation permeability (which correlates to the pore throat sizes in the formation) may readily be determined using rock samples taken during drilling and the optimum impregnated particle size may thus be determined. Since the particles produced as described in EP-B-3905, U.S. Pat. No. 4,530,956 and WO 99/19375 have a very low dispersity (i.e. size variation), a highly uniform deposition and deep penetration into the formation can be achieved. For this reason, the particles preferably have a coefficient of variation (CV) of less than 10%, more preferably less than 5%, still more preferably less than 2%.

CV is determined in percentage as $$CV = 100 \times \frac{\text{standard deviation}}{\text{mean}}$$

where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyser.

For placement in filters, the impregnated particles preferably have mode particle sizes of 50 to 5000 µm, more especially 50 to 1000 µm, still more preferably 100 to 500 µm. In such filters, the impregnated particles preferably constitute 1 to 99% wt, more preferably 2 to 30% wt, still more preferably 5 to 20% wt of the particulate filter matrix, the remaining matrix comprising particulate oil- and water-insoluble inorganic material, preferably an inorganic oxide such as silica, alumina or alumina-silica. Particularly preferably, the inorganic oxide has a mode particle size which is similar to that of the impregnated polymer particles, e.g. within 20%, more preferably within 10%. As with the in-formation placement, the impregnated particles preferably have low dispersity, e.g. a CV of less than 10%, more preferably less than 5%, still more preferably less than 2%. The low dispersity serves to hinder clogging of the filters.

The pores of the particles will be large enough to allow the microorganisms to penetrate without difficulties e.g. a pore radius of up to 2-4 µm.

The impregnated particles are preferably particles having a pore volume of at least 50%, more preferably at least 70%, e.g up to at least 85%.

The bacterially impregnated polymer particles used according to the invention, e.g. MPP or other step-grown polymer particles are preferably vinyl homo- and copolymers more preferably styrenic homo- and copolymers. Examples of appropriate monomers include vinyl aliphatic monomers such as esters of acrylic and methacrylic acids, acrylonitrile, and vinyl aromatic monomers such as styrene and substituted styrenes. Preferred polymers are styrenic polymers, optionally and preferably cross-linked, e.g. with divinyl benzene, and particles of such polymers are commercially available in a range of sizes and pore volumes from Dyno Specialty Polymers AS of Lillestrøm, Norway. If desired, the particles may be functionalised, e.g. to provide surface acidic or basic groups (e.g. carboxyl or amino functions), for example to scavenge metal atoms from water reaching the particles so as to reduce scale formation, to promote particle adhesion to formation surfaces, to promote or hinder particle aggregation, etc. Again functionalised particles are available from Dyno Specialty Polymers AS.

Preferably the polymer matrix of the impregnated particles has a softening point above the temperatures encountered down hole, e.g. one above 70° C., more preferably above 100° C., still more preferably above 150° C.

Generally where the particles are impregnated with bacteria, they will also be impregnated with nutrients for the bacteria, e.g. sucrose, so that bacterial growth is promoted once the particles encounter water. Alternatively, so called "ultra microbacteria" may be used which are "starved" during the injection stage making them easier to penetrate deep into the formation.

Subsequent administration of nutrients will then stimulate growth.

Examples of typical well treatment chemicals, precursors and generators are mentioned in the patent publications mentioned herein, the contents of all of which are hereby incorporated by reference.

Thus for example typical scale inhibitors include inorganic and organic phosphonates (e.g. sodium aminotrismethylenephosphonate), polyaminocarboxylic acids or copolymers thereof, polyacrylamines, polycarboxylic acids, polysulphonic acids, phosphate esters, inorganic phosphates, polyacrylic acids, inulins (e.g. sodium carboxymethyl inulin), phytic acid and derivatives (especially carboxylic derivatives) thereof, polyaspartates, etc.

The use of environmentally friendly scale inhibitors, e.g. inulins, phytic acid and derivatives thereof and polyaspartates, is especially preferred.

Where the scale inhibitor is a polymer it may of course contain residues of one or more different comonomers, e.g. a copolymer of aspartic acid and proline.

Other beneficial microbial products include enzymes which are themselves able to synthesize well treatment chemicals such as scale inhibitors. It may be necessary to transform the bacteria with a plurality of genes coding for different enzymes which are involved in a synthetic pathway for a described well treatment chemical. Thus the well treatment chemical may be directly produced by the Archea, i.e. an expression product, or indirectly produced as a result of metabolism or catabolism within the Archea. Thus the well treatment chemical may be proteinaceous e.g. a polypeptide or glycoprotein but it need not be and could be a polysaccharide or a lipid.

In a particularly preferred embodiment, the well treatment chemical may have a dual function. This can be readily achieved, for example by production of a fusion protein which may have a scale inhibiting part and a part which acts, for example, as a corrosion inhibitor, biosurfactant or antifreeze. Polyaspartate is particularly useful as it can act as scale inhibitor and a corrosion inhibitor.

Examples of preferred well treatment chemicals include: hydrate inhibitor, scale inhibitors, asphaltene inhibitors, wax inhibitors and corrosion inhibitors. Such inhibitors are well known to those working in the field of well treatment.

In certain special circumstances, for example if problems are encountered with carbonate scale or organic naphthenate precipitation, it may be appropriate to introduce the microorganisms discussed herein into the injection well. Thus in a further aspect, the present invention also provides a method for the treatment of a hydrocarbon well which method comprises administering down an injection well thermophilic Archea or other thermophilic bacteria or microorganisms capable of generating well treatment chemicals. Preferred features of this aspect, including the use of Archea which have been genetically modified to produce well treatment chemicals, are discussed above. The microorganisms introduced into the injection well may advantageously produce organic acids and/or chemicals involved in hydrate inhibition.

Where the bacteria are placed within the formation, they are preferably applied as a dispersion in a liquid carrier. For pre- and post-completion application, the liquid carrier preferably comprises a non-aqueous organic liquid, e.g. a hydrocarbon or hydrocarbon mixture, typically a $C_3$ to $C_{15}$ hydrocarbon, or oil, e.g. crude oil. For curative treatment, i.e. after production has continued for some time, the liquid carrier may be aqueous or non-aqueous.

Impregnation of the bacteria and if desired nutrients and/or other well treatment chemicals into porous carrier particles may be effected by any conventional manner, e.g. by contacting the particles with an aqueous or non-aqueous dispersion of the bacteria or other chemicals followed if necessary by solvent removal, e.g. by draining, drying or under vacuum.

However it is especially preferred to impregnate particles with the bacteria by slurry mixing, i.e. by adding a quantity of dispersion which is close to the pore volume of the particles, e.g. 0.8 to 1.2 times pore volume more preferably 0.9 to 1.1 times pore volume. Still more preferred is to impregnate the particles by a soaking procedure using a vacuum. The process may conveniently be performed in a rotavapor at 0-15 mbar at room temperature and continued at 50° C. until most of the water-phase has been removed. It is desirable to introduce bacteria into the pore system not only onto the surface. If desired particle loading may be increased by carrying out more than one impregnation step.

Various methods can be envisaged to sustain the microorganism population in situ. The microorganism can be immobilised in the porous matrix with nutrition packages or co-injected with nutrients into small porous particles which can then be injected deep (e.g. 2-10 m) into the formation. High concentration inoculates of the thermophilic bacteria can be introduced into the porous particles. Advantageously, some of the bacterial species which may be introduced are capable of producing viable spores in the well environment.

The invention also includes a bioreactor for synthesising well treatment chemicals. The well treatment chemicals are thus made in the bioreactor and then applied to the hydrocarbon well. In a preferred embodiment, particles of the type described herein, i.e. porus impregnatable particles may be loaded with the products of the bioreactor. The bioreactor, which may be situated at or near the site of the borehole or remote from the borehole, may function to enable the production of any well treatment chemical, such as those described above. Preferably the bioreactor may enable the production of peptidic scale inhibitors such as poly (amino acids) e.g. polyAsp or other predominantly (positively) charged polypeptides suitable for use as well treatment chemicals. The organisms used in the bioreactor may be naturally occurring, e.g. naturally occurring bacteria or Archea, as exemplified above that product well treatment chemical products are synthesised either though modifying or adding regulatory or structural sequences. It is not necessary to use thermophilic species if a bioreactor is used. Any microorganisms may be used e.g. E. Coli.

Bioreactor as used herein refers to any system for the growth of cells in culture, namely microorganisms such as bacteria or Archea. Nutrients can be supplied to the bioreactor and samples easily removed.

The product isolated from the organisms may be secreted or may be retained in the cell. In the case that the produce is secreted, it may be continuously removed from the cell culture medium, by removing the culture medium and replacing it with the fresh growth medium. The product may then be isolated from the growth medium using standard techniques. Alternatively, the microorganisms may be removed from the bioreactor and the product isolated following cell disruption, using techniques known in the art.

In order to aid isolation of the product, in the case that it is an exogenous protein, the protein may be modified to assist isolation e.g. labelled using a tag, such as a his tag or a myc tag. Such tags and isolation techniques are well known in the art.

The products made in the bioreactor e.g. peptidic scale inhibitors such as polyAsp are either isolated from lysed microorganisms or are secreted and isolated from the growth medium. It may be necessary to add sequences that encode amino acid signals that direct the secretion of the protein under certain circumstances. Irrespective of the mode of production, the product can then be mixed into the general formulation necessary for a traditional squeeze treatment.

Bioreactors thus provide an environmentally friendly system for the production of well treatment chemicals. A further aspect of the invention therefore is the use of a bioreactor to produce well treatment chemicals. Preferably the well treatment chemicals are peptidic scale inhibitors, or other substances that are useful down hole, including charged peptides. Most preferably the charged peptide is polyAsp or a copolymer of aspartic acid and another amino acid as previously defined herein.

The invention will now be described further with reference to the following non-limiting Examples and the figures in which:

FIG. 1 gives a schematic representation of the plasmid pET11d-Aspartate described in Example 2, this plasmid encodes polyAsp and may be used to transform microorganisms as described herein.

EXAMPLE 1

Cloning of Gene for Polyaspartate (PA)

A pET E. Coli expression system was used. This system has a strong selectivity of the bacteriophage T7 RNA polymerase for its cognate promotor sequences, the high level of activity of the polymerase and the high efficiency of translation mediated by the T7 translation initiation signals.

Oligonucleotide for PA

Codon preference for PA was investigated in the "Codon usage database" (http://www.kazusa.or.jp/codon/) before synthesis. PA nucleotide was synthesised with the sequence ----GATGATGAT--- 75 base pairs (25 amino acids), in addition to start and stop codons and specific sequences for ligation into vector after digestion with restriction enzymes (Euro GenTec).

Preparation of Vector and Oligonucleotides

Vector pET 11a (1 g/ml; Stratagene, La Jolla, Calif., USA) was digested with the restriction enzyme NdeI (37° C. overnight). The vector was treated with "calf intestinal alkaline phosphatase" (CIAP; Stratagene) as described by the manufacturer. The vector was then separated by agarose gel electrophoresis (1% agarose), sliced from the gel and purified by gel extraction reagents (Qiaquick gel extraction kit, Qiagen, GmbH, Hilden, Tyskland).

oligonucleotides (100 μmol/l) were heated (95° C., 5 min), the temperature was subsequently reduced by 1° C./min until 65° C. and the sample placed on ice before ligation.

A ratio between vector and insert as recommended by the manufacturer was used.

Ligation and Transformation

Ligation was performed overnight at 18° C. using several ratios between vector and insert. T4 DNA ligase and 10× ligase buffer (pH 7.6) were used.

The ligation mixture was transformed into E. coli DH5 with a "heat-shock" protocol: A ligation mixture was applied to the competent cells (50 1), incubated on ice (30 min), placed on a heating block at 42° C. (45 seconds), and finally on ice (2 min). The cells were then inoculated in LB-medium, incubated in a shaking incubator (37° C., 3 hours) and spread on LB-agar with x-gal, ITPG and ampicillin for selection of clones. LB-plates were incubated at 37° C. overnight.

Isolation and Sequencing of Plasmid DNA

White pigmented clones were picked from the LB-agar, inoculated in LB-broth with ampicillin, and incubated in a shaking incubator overnight (37° C.). Plasmid DNA was isolated with Wizard Plus SV Miniprep DNA purification system (Promega, Madison, Wis., USA) as described by the manufacturer. Sequencing of plasmid DNA was performed with "Big Dye" sequencing reagents (Applied Biosystems, Foster City, Calif., USA), and with T7 promotor primer in the reaction. DNA was precipitated in ethanol and analysed in an ABI Prism DNA377 Sequencer (Applied Biosystems).

EXAMPLE 2

This Example also uses the pET E. Coli system described in Example 1.

Oligonucleotide for PA

Oligonucleotides A 5'-CATGGATGACGATGATGACCCG-GATGATGACGACGATGACGATGACGATCCGGACG ATGACGACGATGATGACGATGATCCTAG-GCATCACCATCACCATCATTAAG-3' and B 5'-GATCCTTAATGATGGTGATGGTGATGC-CTAGGATCATCGTCATCATCGTCGTCATC GTCCG-GATCGTCATCGTCATCGTCGTCATCATC-CGGGTCATCATCGTCATC-3' were synthesised by EuroGen Tec.

Equal quantities of each oligonucleotide were annealed by mixing together heating to 95° C. and allowing the mixture to cool at 1° C./minute to 65° C. The mixed oligonucleotides were then placed on ice. This forms a double stranded DNA with sticky ends compatible with the restriction enzyme sites NcoI and BamHI. Such that directional cloning of the dsDNA insert was possible.

Preparation of Vector

Vector pET11d (Stratagene) was digested with the restriction enzymes BamHI and NcoI according to the manufacturer's instructions to ensure complete digestion. The vector was treated with CIAP as described by the manufacturer. The digested vector was then separated from the excised fragment by agarose gel electrophoresis and purified by gel extraction.

Ligation

For ligation, several ratios between vector and insert as recommended by the manufacturer was used.

Ligation was performed using T4DNA ligase and 10× ligase buffer (pH7.6). The reaction was performed overnight at 18° C., according to standard techniques. The resulting vector is shown in FIG. 1.

The ligation mixture was transformed into (DH10B) *E. coli* cells using a standard "heat-shock" protocol. The transformed cells were then incubated, plated and selected.

Plasmid DNA was isolated from the *E. Coli* and sequenced as described in Example 1 to verify the presence of the insert and its sequence.

EXAMPLE 3

Poly Aspartate Expression and Isolation

Purified plasmid DNA is transformed into *E. Coli* ER2566, which express the T7 DNA polymerase, under the control of a lac promotor. The transformed *E. Coli* are ultured in 3XLB medium, containing ampicillin (200 µg/ml) for 7 hours, with shaking. The expression of polyAsp is induced in one culture after 3 hours by the addition of IPTG to a final concentration of 1 mM. A further culture is left uninduced for comparison purposes. The culture may be incubated at a lower temperature following induction, in order to increase the efficiency of induction. The cells are harvested and resuspended in one-tenth volume of 10 mM Tris pH7.5 and sonicated. The resulting mixture is centrifuged to separate cell debris and the supernatant filtered. Aliquots of the culture medium, sonicated cells and filtrate are taken for analysis, to ascertain whether peptide is secreted or retained in the cell or present as a soluble intracellular/periplasmic protein.

The protein samples are separated using standard polyacrylamide gel electrophoresis, using a 15%-20% polyacrylamide gel. A band at approximately 5 kD indicates the presence of the desired product.

If necessary, the product can be detected using standard immuno blotting techniques such as western Blots, using antibodies directed to polyAsp onto any appropriate protein tag.

EXAMPLE 4

Identification of Archea and Bacteria indigenous to oil fields. These microorganisms may then be used to treat a hydrocarbon well as they are or preferably they are genetically modified to produce a useful well treatment chemical such as polyAsp.

1. Materials and Methods 1.1 Sample Collection and Processing 1.1.1 Sampling

Sterilized 5-L sample glass bottles (Schott) with 5 ml of 0.1% (wt/vol) resazurin reducing agent (Sigma Chemical Co., St. Louis, Mass., USA) per bottle were shipped to the offshore fields. Samples were collected as raw production fluid (oil/water) from the production flow-line before produced water separation. Bottles were completely filled. The top oil layer sealed the water from the atmosphere, eliminating oxygenation of the water phases.

Samples were sent onshore in sealed Al-boxes (transport periods 1-2 weeks). During transportation the boxes were kept at ambient temperature.

No traces of oxygen were detected in the water phases when the samples arrived onshore.

1.1.2 Filtration of Water Samples

After arrival at the laboratory the oil and water phases of the production fluid samples were immediately heated (70° C.; 20 minutes) and the hot phases separated in 2 L separating funnels (2 L). Microbial biomass from 1-2 L water was collected by filtration through 0.22 µm Sterivex GV filters (Millipore Corp., Bedford, Ma, U.S.A) connected to Millex AP prefilters (Millipore). After filtration each Sterivex filter was filled with a 2 µl lysis buffer (50 mM Tris-HCl, pH 8.0; 40 mM EDTA; 750 mM sucrose) and stored at −20° C. until DNA extraction.

One of the samples was highly emulsified, resulting in only a small water phase. This emulsion phase was washed with a sterile buffer solution, phase separated, and filtered (approximately 1 L buffer phase) as described above.

1.2 Cell Counts

Cell numbers in water phases of the production fluids were enumerated immediately after the arrival at the laboratory by epifluorescence microscopy. Samples were prefiltered (Millex AP, Millipore), and 100 ml filtrates centrifuged (6000×g; 10 minutes to remove coarse particles and residual oil droplets. The fluorochrome 4'6-diamino-2-phenylindol (DAPI; 0.6 µg/ml) was applied to the supernatants (10 ml), and the samples incubated at room temperature (10 minutes), followed by filtration through 0.22 µm black polycarbonate filters (Millipore). The filters were mounted in a fluorescence microscope (Leitz Dialux with Ploemopak fluorescence unit and UV-filter A and equipped with a Leica DC 100 digital camera) with immersion oil. Fluorescent cells were enumerated with 1250× magnification.

1.3 Polymerase Chain Reaction (pcr) Amplification of Reservoir Samples 1.3.1 Nucleic Acid Extraction and Quantification The frozen Sterivex filters with microbial communities were thawed and lysed directly on the filters. The lysis was performed by incubation of each filter with 2 µg lysozyme (Sigma; from a 20 mg/ml stock solution; 370 for 30 minutes). The mixtures were then incubated at 55° C. for 2 hours with 1 µg Proteinase K (Sigma; from a 20 mg/ml stock solution), and 1% (wt/vol) sodium dodecyl sulphate (SDS; BioRad Labs, Richmont, Calif., USA) from a 20% stock solution.

The lysates were transferred to sterile tubes, the Sterivex filters washed with lysis buffer (55° C.; 10 minutes), and the lysates from each filter pooled. The lysates were extracted with hot phenol-chlorophorm-isoamylalcohol (25:24:1) according to standard procedures (Sambrook and Russel, 2001). Briefly, each lysate (3 ml) was mixed with 6 ml hot (60° C.) Tris-HCl buffered phenol-chlorophorm-isoamylalcohol (pH 8.0), vigorously shaken, maintained hot for 5 minutes, then cooled on ice, followed by phase separation by centrifugation (4000×g; 5 minutes at 4° C.; Jouan Model 1812, Saint Nazaire, France). Sodium acetate (0.2 volume of 10 M solutions) was applied to each water phase, and these were re-extracted with 5 ml Tris-HCl buffered phenol-chlorophorm-isoamylalcohol, followed by centrifugation. The water phases were then extracted with 5 ml hot (60° C.) chlorophorm-isoamylalcohol (24:1), and centrifuged as described above. The extracted water phases were precipitated by 2.5 volumes of 96% ethanol (−20° C.; 3 hours), the precipitates pelleted by centrifugation (4000×g), and the pellets washed with 75% ethanol. The pellets were dried ($N_2$) after re-centrifugation and dissolved in 100 µl sterile ultra-pure water (Biochrom AG, Berlin, Germany). The nucleic acid extracts were frozen (−20° C.).

Extracted nucleic acids were semi-quantified with an ethidium bromide method (Sambrook and Russel, 2001). Nucleic acids (2 µl) were spotted on a UV transilluminator table (BioRad) wrapped with plastic film ("GladPak"), and 2 µl ethidium bromide (10 mg/ml in TE buffer, pH 8.0) were applied to each spot. The spots were photographed under UV-illumination and concentrations determined by intensity comparison to a standard series of salmon DNA (Sigma) in the range 100-5.00 ng DNA per spot.

1.3.2 Oligonucleotides and PCR Reagents 1.3.2.1 Oligonucleotides for PCR Amplification Oligonucleotide primers were prepared specific for Bacteria and Archea (Teske et al., 1996; DeLong, PNAS USA 89(1):5685-9, 1992):

Bacteria

341fBac: 5'-CCT-ACG-GGA-GGC-AGC-AG-3' (forward primer)

907rBac: 5'-CCC-CGT-CAA-TTC-CTT-TGA-GTT-3' (reverse primer)

Expected PCR product: 567 bp

Archea

21fARCH: 5'-TTC-CGG-TTG-ATC-CCG-CCG-GA-3' (forward primer)

958rARCH: 5'-CCC-GGC-GTT-GAA-TTC-AAT-T-3' (reverse primer)

Expected PCR product: 938 bp

The primers were synthesized by EuroGentec, Seraing, Belgium. The primers were diluted in sterile water at concentrations of 50 µM, distributed in 50 µl aliquots and stored at −20° C.

1.3.2.2 Biotinylated Oligonucleotides

A number of biotinylated DNA oligonucleotides (5'- and 3'-labelled) were prepared (Teske et. al., 1996; Massana et. al., 1997) for Southern blotting analysis of PCR products:

δ subdivision/gram-positive bacteria (included *Desulfovibrio* and *Desulfobulbus*)

385 SRB: Biotin-5'-CGG-CGT-CGC-TGC-GTC-AGG-3'-Biotin

Hybridization temperature: 50° C.

Desulfobacter and Desulfobacterium

804 SRB: Biotin-5'-CAA-CGT-TTA-CTG-CGT-GGA-3'-Biotin

Hybrization temperature: 40° C.

Crenarchaeota (Group I Archea)

554 ARCH-I:

Biotin-5'-TTA-GGC-CCA-ATA-ATC-MTC-CT-3'-Biotin

Hybrization temperature: 40° C.

Euryarchaeota (Group II Archea)

554 ARCH-II:

Biotin-5'-TTA-GGC-CCA-ATA-AAA-KCG-AC-3'-Biotin

Hybrization temperature: 40° C.

All biotinylated primers were synthesized by EuroGentec, Seraing, Belgium. The primers were diluted in sterile water at concentrations of 50 µM, distributed in 50 µl aliquotes and stored at −20° C.

1.3.2.3 Deoxynucleotides

Stock solutions of deoxynucleotides (d'NTP) were prepared by diluting 100 mM of the d'NTPs 2'-deoxyadenosine 5'-triphosphate (d'ATP), 2'-deoxythymidine 5'-triphosphate (d'TTP), 2'-deoxyguanosine 5'-triphosphate (d'GTP) and 2'-deoxycytidine 5'-triphosphate (d'CTP) (Amersham Pharmacia Biotech, Piscataway, N.J., U.S.A). Each d'NTP (100 µl) was diluted in sterile water (600 µl), resulting in final concentrations of 10 mM of each d'NTP. Solutions were distributed in 50 µl aliquots and stored at −20° C.

1.3.3 Touchdown PCR

Extracted DNA (see above) or lysed microbial cell suspensions were used as DNA template for PCR amplification. When lysed cell suspensions were used broth cultures were diluted in sterile water ($10^{-2}$) or colonies from agar plates suspended in sterile water, followed by heating (100° C.) in 10 minutes.

A PCR mix of 100 µl mix consisted of 20 µl d'NTP (10 mM), 10 µl forward primer (50 µM), 10 µl reverse primer (50 µM), 55 µl sterile water and 5 µl AmpliTaq DNA polymerase (Perkin Elmer Roche Molecular Systems, Branchburg, N.J., U.S.A).

DNA template (1-10 µl) was diluted in 10 µl [10×] PCR buffer with 15 µM $MgCl_2$ (Perkin Elmer Roche) and with sterile water to a final volume of 90 µl. The mixture was heated (95° C.) in 5-10 minutes on a heating block. A PCR mix of 10 µl was applied to each sample when the samples were still in the heating block (95° C.) and the samples were immediately transferred to a DNA Thermal Cycler (icycler, BioRad).

PCR was run as a touchdown method to reduce the generation of spurious by-products, and with the following sequence cycles:

Denaturation: 95° C. for 1 minute

Primer annealing: 65-55° C. for 1 minute

DNA synthesis (primer extension): 72° C. for 3 minutes

Number of cycles: 35

During the first 10 cycles the annealing temperature was gradually reduced from 65 to 55° C. with 1° C. for each cycle during the first 10 cycles, followed by 25 cycles with annealing temperature of 55° C. The PCR runs were terminated by 72° C. for 15 minutes before cooling to 4° C.

1.3.4 Agarose Gel Electrophoresis 1.3.4.1 Analytical Electrophoresis

PCR products were analysed by horizontal agarose gel electrophoresis. Samples (27 µl) were mixed with [10×]

gel-loading TBE buffer (3 µl) (0.9 M Tris, 0.9 M borate, 20 mM EDTA, pH 8.3, 50% (v/v) glycerol, 0.25% (w/v) bromophenol blue). A Low DNA Mass Ladder (Gibco BRL, Paisley, UK) was used as standard, 12 µl standard in 3 µl [10×] gel-loading TBE buffer.

Gels were prepared by heating agarose (2.0 g; Sigma) in 160 ml [0.5×] TBE (0.045 M Tris, 0.045 M borate, 1 mM EDTA, pH 8.3) in a microwave oven (4 minutes), followed by cooling to 50° C. in water bath. Ethidium bromide (10 µl) from a stock solution (10 mg/l ethidium bromide in sterile water) was applied to the agarose, and the melted gel was casted horizontally in a plastic tray (open ends of the tray sealed) with a comb of 15-well or 20-wells in the electrophoresis apparatus (BioRad). The gel was set at room, temperature for 20 minutes, submerged in [0.5×] TBE buffer, and the comb and seals carefully removed.

Prepared samples and standard (see above) were applied to the submerged gel wells (20 µl sample and 10 µl standard) and electrophoris run with constant voltage (150 V) for 1.5-2 hours at room temperature. Gel documentation was performed over a UV-transilluminator table (BioRad). The gels were photographed by black-white Polaroid film (0.1-0.5 second exposure time), or by digital camara (GelDoc, 2000, BioRad).

1.3.4.2 Preparative Electrophoresis

Preparative agarose gel electrophoresis was performed basically as described above for the analytical approach, except that a low-melt agarose (Sigma) was used. Agarose (1.3 g) was melted in 160 ml [0.5×] TBE buffer or [1×] TAE buffer (0.04 M Tris-acetate, pH 8.0; 1 mM EDTA), the gel solution cooled to 35-500, ethidium bromide applied, and the horizontal gel as described above, except that the set temperature was 4-5° C. Samples were applied as described above, and electrophoresis run at 100 V constant voltage for 1.5-2 hours.

After electrophoresis the gels were photographed and selected DNA bands cut out from the agarose with a sterile scalpel and transferred to microcentrifuge tubes. Before further processing the agarose slices were pelleted with a brief centrifugation and melted at 65° C. for 15 minutes. The samples were maintained melted at 35-37° C.

1.3.5 Southern Blotting and hybridization 1.3.5.1 Blotting

By Southern blotting agarose gel electrophoresis of PCR products were performed as described above (analytical approach), except that no ethidium bromide was added to the gel. DNA was transferred from the gel to Hybond N+ membranes (Amersham Pharmacia) by diffusion blotting.

After electrophoresis the gel was soaked in 10 volumes of denaturation solution (0.5 M NaOH, 1.5 M NaCl) for 2×20 minutes (slow agitation), followed by neutralization (1 M ammonium acetate) for 2×15 minutes. The gel was then trimmed and placed on a glass plate with chromatographic paper (3 mm Chr, Whatman, Maidstone, U.K.) soaked in 1 M ammonium acetate. The ends of the chromatographic paper was placed into a bath of transfer buffer (0.2 M ammonium acetate). The gel was surrounded by a thin plastic film ("GladPak") to prevent transfer buffer evaporation. The Hybond N+ transfer membrane was soaked in 0.2 M ammonium acetate and placed tightly on the top of the gel. Several layers of chromatographic paper (soaked in 0.2 M ammonium acetate) were placed on the top of the membrane, and a stack of paper towels (5-8 cm) was placed on the top of the chromatographic papers. A glass plate with a weight (300-400 g) was placed on the top of the paper towels.

The DNA transfer was performed overnight (8-12 hours) at room temperature, and the paper towels were changed when they became wet. The blotting quality was controlled by staining the gel in a bath of ethidium bromide (0.5 µg/ml in water) for 45 minutes. After blotting DNA was fixed to the Hybond membrane under UV light for 40 seconds. The membranes were hybridized immediately or wrapped in plastic and stored (dark) at 4° C.

1.3.5.2 Hybridization

Before hybridisation fixed membranes were prehybridised in a solution (10 ml) of 3×SSC, 0.10 SDS and 1.0% Blocking agent (Roche Molecular Biochemicals) for 2 hours at the selected hybridisation temperature for the different DNA probes (see above) in a Roller-Blot HB-3D hybridiser (Techne, Cambridge, UK). Biotinylated DNA-probes were then applied to the roller bottles in the hybridiser and incubated at 16-20 hours at the temperatures described for the different DNA-probes (ses above).

After hybridisation the membranes were washed 10 minutes in 50 ml 2×SSC—0.1% SDS, 10 minutes in 50 ml 0.1×SSC—0.1% SDS, and 10 minutes with PBS-T (all washes at room temperature). The membranes were incubated with Extravidin-Peroxydase (Sigma Chemical Co., St. Louis, Mo.), diluted 1:2000 i PBS-T for 30 minutes at room temperature (agitation), washed 2×10 minutes with PBS-T, 10 minutes with PBS (room temperature), and developed (10-20 minutes) in 30 ml PBS with 2 tablets diaminobenzidine (DAB; Sigma) and 24 ml 300 water-free $H_2O_2$. After development the membranes were rinsed in tap water and photographed.

1.4 Denaturing Gradient Gel Electrophoresis (DGGE)

1.4.1 Analytical DGGE

By DGGE PCR products were generated with general primers defining Bacteria (341fBAC and 907rBAC) or Archea (21fARCH and 958rARCH). To the primers 341f BAC and 21fARCH a 40 mer GC-clamp was added to the 5'-end (5'-CGC-CCG-CCG-CGC-GCG-GCG-GGC-GGG-GCG-GGG-GCA-CGG-GGG-G-3').

DGGE was performed with 6% (w/v) polyacrylamide (PAA) gels in [0.5×] TAE buffer (20 mM Tris-acetat, pH 7.4; 10 mM acetat; 0.5 mM EDTA) with a 20-70% gradient of the denaturing agents urea and formamide (100% denaturing agents corresponded to 7 M urea and 40% (v/v) deionised formamide) in a DCode Universal Mutation Detection system (BioRad).

Stock solutions of PAA/Bis-acrylamide (Bis) (40%) consisted of 38.93 g acrylamide and 1.07 g Bis dissolved in deionised water to 100 ml, while stock solutions of [50×] TAE buffer was generated by mixing 242 g Tris, 57.1 g acetic acid, and 100 ml 0.5 M EDTA to a total volume of 1000 ml with deionised water. Linear gradient gels (thickness 1 mm) were prepared by mixing PAA and Bis with denaturating agents to generate a 20 to 70% linear gradient in a gradient delivery system (BioRad modell 475). Solutions with 20% or 70% denaturing agents are described in Table 1 below:

TABLE 1

Composition of 20% and 70% denaturating solutions used in DGGE

| | Denaturating Solutions | |
|---|---|---|
| CHEMICALS | 20% | 70% |
| 40% acrylamide/Bis | 15 ml | 15 ml |
| [50x]TAE buffer | 2 ml | 2 ml |

TABLE 1-continued

Composition of 20% and 70% denaturating solutions used in DGGE

| CHEMICALS | Denaturating Solutions | |
|---|---|---|
| | 20% | 70% |
| Formamide | 8 ml | 28 ml |
| Urea | 8.4 g | 29.4 g |
| Deionised water | to 100 ml | to 100 ml |

For the preparation of one gel 18 ml of each solution was mixed with 200 ml ammonium persulphate (10% (w/v) in deionised water) and 20 µl TEMED (BioRad), and the mixtures immediately transferred to each of two 30-ml syringes which were subsequently mounted in the gradient delivery system. The gel was cast as a parallel gradient gel (16×16 cm) with 1 mm thickness and allowed to polymerize for approximately 1 hour, and with a comb of 15 wells. The electrophoresis tank was filled with [1×] TAE buffer which was heated to 60° C. in the tank, and 1-2 polymerised gels placed vertically in the electrophoresis tank.

Each PCR product sample (10 µl) was mixed with 10 µl sample buffer (0.05% bromophenol blue, 0.05% xylene cyanol, 70% glycerol, diluted in deionised water), and the complete volume (20 µl) applied to each well.

Vertical electrophoresis was performed with continuous temperature (60° C.) and voltage (150 V) until the both markers had migrated to the bottom of the gel (approximately 4.5 hours).

After electrophoresis the gels were stained in SYBR Gold (Molecular Probes, Leiden, The Netherlands), diluted 1:10,000 in [1×] TAE. for 20-30 minutes. The gels were then photographed with the GelDoc system (BioRad).

The gel band patterns were compared for similarity and similarity indices generated by the Quantity One option of the GelDoc software program. The Dice Coefficient method was used, based on the following formula for similarity:

$$\text{Similarity} = 200 \times \frac{\sum_{i=1}^{B} \text{Min}(s_p t_j)}{\sum_{i=1}^{B} (s_j t_j)},$$

where S and T are vectors representing two lanes in the same band set that are being compared.

1.4.2 Preparative DGGE

Preparative DGGE was performed as described for the analytical DGGE, except that N,N'-bis-acrylylcystein (BAC; Sigma) was used instead of Bis during gel generation. The BAC enabled gel solution after electrophoresis (Muyzer et al., 1996).

PCR samples (300 µl) were precipitated with 30 µl of 5 M NaCl and 750 µl ethanol at −80° C. for 1 hour, centrifuged (20 000×g, 2 minutes) in a microcentrifuge (Eppendorf Model 5417C, Eppendorf, Hamburg, Germany). The pellet washed with 70% ethanol, dried on a heating block (35° C., 20 minutes) and dissolved in 30 µl sterile water.

The gel was cast, samples applied, and electrophoresis run as described above.

The gel was stained after electrophoresis with SYBR Gold (see above), and selected bands cut under UV-illumination with sterile scalpels. Each slice of gel was transferred to a microcentrifuge tube, washed 2×10 minutes with 100 µl sterile water, and the water removed. β-mercaptoethanol (100 µl; BioRad) was applied and the tubes incubated for 16-20 hours at 37° C. Deionised water (100 µl), 0.1 volume 5 M NaCl, and 2.5 volumes ice cold ethanol was applied to each tube. The tubes were incubated at −80° C. for 2 hours, centrifuged (10 000×g, 20 minutes) in a microcentrifuge, and the supernatant removed carefully. The tubes were dried (35° C., 20 minutes), and the pellet was dissolved in 100 µl sterile water.

PCR product content in the samples was checked in PCR with primers defining Bacteria, but without GC-clamp. The PCR products were then purified in preparative agarose gel electrophoresis with low-melting temperature agarose (see above).

1.5 Cloning

1.5.1 TOPO TA Cloning

Cloning was performed with the TOPO TA Cloning kit (Invitrogen, Carlsbad, Calif., U.S.A), with the pCR 2.1-TOPO plasmid vector and One Shot TOP10 chemically competent *Escherichia coli* cells.

DNA was amplified in PCR using 341fBAC and 907rBAC primers defining Bacteria. PCR was performed as described above (see section 3.4.3), except that the final termination at 72° C. was prolonged to 10 minutes to generate 3'-adenine overhangs. The PCR products were purified in preparative agarose gel electrophoresis with low-melting temperature agarose as described above (see section 3.4.4.). The gel slices with PCR products were melted as described (65° C., 15 minutes) and maintained melted at 370 until ligated into the vector.

Melted agarose slices (4 µl) were carefully mixed with 1 µl salt solution (1.2 M NaCl, 0.06 M MgCl$_2$) and 1 µl TOPO pCR 2.1 vector. The ligation was performed for 10 minutes at 37° C. The tubes were placed on ice, and transformation of the vector (4 µl) into chemically competent TOP10 cells (50 µl) performed on ice (15 minutes), followed by heat-shock (42° C., 30 seconds), and immediate transfer to ice (10 minutes). The transformation reaction was diluted in 250 µl SOC medium (2% Tryptone, 0.5% yeast extract, 10 mM NaCl, 2.5 mM KCl, 10 mM MgCl$_2$, 10 mM MgSO$_4$, 20 mM glucose), and the reaction in a shaking incubator at 37° C. for 1 hour with 200 rpm horizontal shaking.

The suspensions were spread on agar plate with Luria-Bertani (LB) agar medium (1.5% agar, 1.0% Tryptone, 0.5% yeast extract, 1.0% NaCl, pH 7.0; Sigma) supplemented with 50 µg/ml ampicillin or kanamycin antibiotics. Before inoculation the plates were spread with X-gal (5-bromo-4-chloro-3-indolyl b-D-galactopyranoside; Sigma), 40 µl of 40 mg/ml X-gal in dimethylformamide.

Suspensions (20 and 50 µl) of transformants were spread on the LB agar plates (20 µl suspensions were diluted with 20 µl SOC medium before plate spreading to ensure even spreading). The plates were incubated for 20-24 hours at 37° C. Only transformants with inserted plasmid grew on the medium, due to the resistance gene of the plasmid. Colonies with PCR products ligated into the vector were visualised as white colonies, opposed to light or dark blue colonies with vectors without PCR product inserts. Discrete white colonies were isolated in liquid LB medium, supplemented with ampicillin or kanamycin (50 µg/ml). The medium was distributed in 24-well sterile tissue culture plates (Corning Inc., Corning, N.Y., USA), with 2 ml medium/Well. The clones were incubated 20-24 hours in the LB medium, and the plasmids purified.

1.5.2 Isolation of Plasmids

The plasmids were isolated with a GenElute Plasmid Miniprep kit (Sigma), according to the instructions from the manufacturer. Transformant clones (2 ml) were harvested by centrifugation on a microcentrifuge (Eppendorf) at 14 000×g for 2 minutes. The pellets were resuspended in a Resuspension Solution (200 μl) by vortexing. A Lysis Solution (200 μl) was added, the mixture gently inverted until clarification (8-10 times), and the lysis neutralized within 3-5 minutes with 350 μl Neutralization/Binding Buffer. The cell debris were pelleted by centrifugation (14 000×g for 10 minutes). The supernatants were transferred into GenElute Miniprep binding columns assembled into microcentrifuge tubes, centrifuged (14 000×g for 2 minutes), and the flow-through liquid discarded. The binding columns were then washed with 750 μl Wash Solution and centrifuged (14 000×g for 2 minutes), effluents discarded, and the columns re-centrifuged (14 000×g for 2 minutes) to remove any additional solutions. The binding columns were then transferred to new microcentrifuge tubes, 100 μl sterile water applied, and the tubes centrifuged (14 000×g for 2 minutes). The isolated plasmid solutions were stored at −20° C.

1.5.3 Control of Positive PCR Insert

Positive PCR inserts in the transformant vector was controlled by PCR with M13 primers defining vector sequences flanking the inserted sequence.

The primer sequences were:

M13 Forward primer (−20): 5'-GTA-AAA-CGA-CGG-CCA-G-3'

M13 Reverse primer: 5'-CAG-GAA-ACA-GCT-ATG-AC-3'

The primer sites corresponded to the bases 391-406 (M13 Forward −20) and 205-221 (M13 Reverse) of the LacZa fragment of the vector. A plasmid without a positive PCR product insert would result in a 202 bp M13 PCR product, while a positive PCR product would result in a 769 bp PCR product.

A PCR mix was prepared as described above (see section 3.4.3) with the M13 primer set (50 μM stock solutions). Plasmid DNA template (2 μl) was diluted in PCR buffer and sterile water to a final volume of 90 μl as described above, mixed with PCR mix. The PCR was run according to the following sequence cycles:

Initial denaturation: 94° C. for 2 minutes

Denaturation: 95° C. for 1 minute

Primer annealing: 55° C. for 1 minute

DNA synthesis (primer extension): 72° C. for 1 minute

Number of cycles: 30

The PCR run was terminated at 72° C. (7 minutes) and cooling at 4° C.

1.5.4 Restriction Fragment Length Polymorphism (RFLP)

M13 PCR products with positive PCR product insert were analysed with the restriction endonucleases EcoRI (Sigma), HaeIII (Sigma) and RsaI (Sigma). The restriction enzymes and corresponding enzymes (provided by the manufacturer; Sigma) is described in Table 2.

TABLE 2

Characteristics of restriction endonucleases and their buffers

| ENZYME | [A] ACTIVITY | RECOGNITION SEQUENCE | DIGESTION BUFFER | BUFFER COMP. (1 X DILUTION) |
|---|---|---|---|---|
| EcoRI | 40000 U/ml | 5'G/AATTC 3' | Buffer SH | 50 mM Tris-HCl<br>100 mM NaCl<br>100 mM MgCl2<br>1 mM dithioerythritol<br>pH 7.5 |
| HaeIII | 10000 U/ml | 5'GG/CC 3' | Buffer SM | 10 mM Tris-HCl<br>50 mM NaCl<br>10 mM MgCl2<br>1 mM dithioerythritol<br>pH 7.5 |
| RsaI | 10000 U/ml | 5'GT/AC | Buffer SL | 10 mM Tris-HCl<br>10 mM MgCl2<br>1 mM dithioerythritol<br>pH 7.5 |

[A] One unit of each enzyme cleaves 1 mg lDNA in 1 hour at 37° C.

Plasmid DNA amplified by M13 PCR (1, 5, or 10 μl) were mixed with restriction enzymes: 1.0 μl EcoRI (40 U), 2.0 μl HaeIII (20 U), or 2.0 μl RsaI (20U). Each mixture was diluted to a total volume of 50 μl with the respective enzyme buffers [1×] concentration (see Table 2). The reaction mixtures were incubated at 37° C. for 2.5 hours and placed on ice to stop the reaction. The enzyme digestion was analysed as restriction fragment length polymorphism (RFLP) on analytical agarose gel electrophoresis.

1.6 Sequencing of Plasmid DNA

For sequencing purified plasmids were PCR amplified with the M13 primer set. DNA was measured by the ethidium bromide method, and precipitated with 60% ethanol and 0.1 M Na-acetate buffer (pH 4.6).

The precipitated PCR-products were submitted for DNA sequencing (MedProbe).

Sequences from the plasmids were submitted to the National Centre for Biotechnology Information (NCBI) using the BLAST program of the NCBI database (Altschul et al., 1997).

Phylogenetic trees and distance matrices were determined with the Phylip interphase of the Ribosomal Database Project (RDP; Maidak et al., 1997).

The invention claimed is:

1. A method for the treatment of a hydrocarbon well, which method comprises administering down a bore hole thermophilic microorganisms which have been genetically modified to generate a well treatment chemical.

2. The method of claim 1 wherein said thermophilic microorganism is also halophilic and anaerobic.

3. The method of claim 2 wherein said thermophilic microorganism is indigenous to the hydrocarbon field in which the well to be treated is located.

4. The method of claim 1 wherein said well treatment chemical is selected from the group consisting of a scale inhibitor, hydrate inhibitor, alsphaltene inhibitor, wax inhibitor and a corrosion inhibitor.

5. The method of claim 1 wherein the well treatment chemical is selected from the group consisting of a protein or peptide molecule, an alcohol, a glycerol, a proteinaceous or non-proteinaceous anti-freeze molecule, biosurfactant and organic acid.

6. The method of claim 5 wherein at least 50% of all amino acids in said protein or peptide have charged side chains.

7. The method of claim 6 wherein said charged amino acids are aspartic acid.

8. The method of claim 7 wherein the well treatment chemical is polyAsp or a copolymer thereof.

9. The method of claim 8 wherein said copolymer is a copolymer of aspartic acid and an amino acid selected from the group consisting of histidine, glycine, alanine, proline, leucine, serine and tyrosine.

10. The method of claim 1 wherein said microorganism is a thermophilic Archea or thermophilic bacteria.

11. The method of claim 10 wherein said thermophilic microorganism is a thermophilic Archea.

12. The method as claimed in claim 1 wherein said bore hole is a producer bore hole.

13. The method of claim 1 wherein said bore hole is an injection bore hole.

14. A method as claimed in claim 1 wherein the well treatment chemical is secreted by the microorganism.

15. The method of claim 1 wherein said microorganisms are delivered to the down hole site in or on particles.

16. The method of claim 15 wherein said particles also carry nutrients for the thermophilic microorganisms.

17. The method of claim 15 wherein said particles have a mode particle size of 1 µm to 5 mm.

18. Particles suitable for administration down a bore hole, said particles being impregnated with thermophilic microorganisms which have been genetically modified to generate a well treatment chemical.

19. Particles as claimed in claim 18 wherein said well treatment chemical is polyAsp or a copolymer thereof.

20. Particles as claimed in claim 19 wherein said copolymer is a copolymer of aspartic acid and an amino acid selected from the group consisting of histidine, glycine, alanine, proline, leucine, serine and tyrosine.

21. A hydrocarbon well treatment composition comprising a carrier liquid containing thermophilic microorganisms which have been genetically modified to produce a well treatment chemical.

22. A composition as claimed in claim 21 wherein said well treatment chemical is polyAsp or a copolymer thereof.

23. The composition of claim 21 wherein said copolymer is a copolymer of aspartic acid and an amino acid selected from the group consisting of histidine, glycine, alanine, proline, leucine, serine and tyrosine.

24. A microorganism genetically engineered to produce a well treatment chemical selected from the group consisting of polyAsp or a copolymer thereof.

25. A microorganism as claimed in claim 24 which is thermophilic.

26. A microorganism as claimed in claim 24 which is an Archea.

27. A microorganism as claimed in claim 24 wherein said copolymer is a copolymer of aspartic acid and an amino acid selected from the group consisting of histidine, glycine, alanine, proline, leucine, serine and tyrosine.

28. The method of claim 24, wherein 30% to 100% of the amino acids in said polyAsp or a copolymer thereof are acidic amino acids.

29. A method of transforming a microorganism which comprises introducing into said microorganism a nucleic acid molecule encoding polyAsp or a copolymer thereof.

30. A method as claimed in claim 29 wherein said microorganism is thermophilic.

31. The method of claim 29 wherein said copolymer is a copolymer of aspartic acid and an amino acid selected from the group consisting of histidine, glycine, alanine, proline, leucine, serine and tyrosine.

32. A bioreactor comprising a culture of microorganisms which have been genetically modified to produce a well treatment chemical selected from the group consisting of polyAsp or a copolymer thereof.

33. A bioreactor as claimed in claim 32 wherein said copolymer is a copolymer of aspartic acid and an amino acid selected from the group consisting of histidine, glycine, alanine, proline, leucine, serine and tyrosine.

34. The method of claim 32, wherein 30% to 100% of the amino acids in said polyAsp or a copolymer thereof are acidic amino acids.

35. A method for the treatment of a hydrocarbon well which comprises harvesting polyAsp or a copolymer thereof from a bioreactor wherein a culture of microorganisms which have been genetically modified to produce polyAsp or a copolymer thereof are producing said polyAsp or a copolymer thereof and then administering said polyAsp or a copolymer thereof down a bore hole.

36. A method as claimed in claim 35 wherein said bore hole is a producer bore hole.

37. A method as claimed in claim 35 wherein said well treatment chemical is delivered down hole in or on particles.

38. The method of claim 35 wherein said copolymer is a copolymer of aspartic acid and an amino acid selected from the group consisting of histidine, glycine, alanine, proline, leucine, serine and tyrosine.

* * * * *